United States Patent
Uehara

(10) Patent No.: US 7,462,585 B2
(45) Date of Patent: Dec. 9, 2008

(54) CONDITIONING COMPOSITIONS COMPRISING COACERVATE AND GEL MATRIX

(75) Inventor: Nobuaki Uehara, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 143 days.

(21) Appl. No.: 11/481,482

(22) Filed: Jul. 6, 2006

(65) Prior Publication Data

US 2007/0010408 A1 Jan. 11, 2007

Related U.S. Application Data

(60) Provisional application No. 60/697,191, filed on Jul. 7, 2005.

(51) Int. Cl.
*C11D 1/62* (2006.01)
*C11D 3/37* (2006.01)

(52) U.S. Cl. .................. 510/123; 510/119; 510/124; 510/130; 510/417; 510/432; 510/434; 510/466; 510/477; 510/504

(58) Field of Classification Search .................. 510/119, 510/123, 124, 130, 417, 432, 434, 466, 477, 510/504
See application file for complete search history.

(56) References Cited

U.S. PATENT DOCUMENTS 4,753,793 A * 6/1988 Walton .................... 424/70.11
5,019,377 A * 5/1991 Torgerson ................. 424/70.16
5,034,218 A * 7/1991 Duvel ....................... 424/70.12
5,853,707 A 12/1998 Wells
6,106,815 A * 8/2000 Kang et al. .............. 424/70.12
6,524,563 B1 2/2003 Wire
6,589,517 B1 7/2003 McKelvey
2001/0027171 A1* 10/2001 Sajac et al. ................. 510/124
2003/0091523 A1 5/2003 Dhandhere
2005/0232888 A1* 10/2005 Weber et al. ............. 424/70.12
2007/0071780 A1* 3/2007 Dubois et al. ............... 424/401

FOREIGN PATENT DOCUMENTS

| EP | 539251 | * | 8/1997 |
| EP | 0539251 B1 | | 8/1997 |
| WO | WO-98/18434 A1 | | 5/1998 |
| WO | 01/76543 | * | 10/2001 |
| WO | PCT/US2006/025862 | | 11/2006 |

* cited by examiner

*Primary Examiner*—Charles I Boyer
(74) *Attorney, Agent, or Firm*—Linda M. Sivik; Marianne Dressman; Taraq M. Rosnell

(57) ABSTRACT

Disclosed are conditioning compositions comprising by weight: (a) from about 0.1% to about 10% of a cationic surfactant; (b) from about 0.05% to about 10% of a water-soluble polymer selected from the group consisting of a water-soluble anionic polymer, a water-soluble amphoteric polymer, and mixtures thereof; (c) from about 1.0% to about 10% of a high melting point fatty compound; and (d) an aqueous carrier; wherein the cationic surfactant and the polymer from a water-soluble complex; and wherein the cationic surfactant and the high melting point fatty compound from a gel matrix. The compositions are especially suitable for hair care products such as hair conditioning products for rinse-off use.

1 Claim, No Drawings

CONDITIONING COMPOSITIONS COMPRISING COACERVATE AND GEL MATRIX

CROSS REFERENCE TO RELATED APPLICATION

This application claims the benefit of U.S. Provisional Application No. 60/697,191, filed on Jul. 7, 2005.

FIELD OF THE INVENTION

The present invention relates to conditioning compositions comprising: a cationic surfactant; a water-soluble polymer selected from the group consisting of a water-soluble anionic polymer, a water-soluble amphoteric polymer, and mixtures thereof; a high melting point fatty compound; and an aqueous carrier; wherein the cationic surfactant and the polymer form a water-insoluble complex; and wherein the cationic surfactant and the high melting point fatty compound form a gel matrix. The compositions are especially suitable for hair care products such as hair conditioning products for rinse-off use.

BACKGROUND OF THE INVENTION

A variety of conditioning compositions such as hair conditioning compositions, skin conditioning compositions, and fabric softeners have been used for a variety of substrates such as hair, skin, and fabric. A common method of providing conditioning benefits is through the use of conditioning agents such as cationic surfactants and polymers, high melting point fatty compounds, low melting point oils, silicone compounds, and mixtures thereof. Most of these conditioning agents are known to provide various conditioning benefits by depositing on the substrates.

However, it is still not easy to obtain expected conditioning efficacy from the conditioning agents. It is not easy to obtain expected deposition of the conditioning agent on the substrates such as hair, skin, and fabric. When styling efficacy is expected in addition to the conditioning efficacy, it is also not easy to obtain such expected styling efficacy, especially improved hair setting.

Based on foregoing, there remains a desire for conditioning compositions which provide improved conditioning benefits. There also remains a desire for conditioning compositions which provide improved styling benefits, in addition to improved conditioning benefits.

None of the existing art provides all of the advantages and benefits of the present invention.

SUMMARY OF THE INVENTION

The present invention is directed to compositions comprising by weight:
(a) from about 0.1% to about 10% of a cationic surfactant comprising at least one cationic surfactant;
(b) from about 0.05% to about 10% of a water-soluble polymer selected from the group consisting of a water-soluble anionic polymer, a water-soluble amphoteric polymer, and mixtures thereof;
(c) from about 1.0% to about 10% of a high melting point fatty compound; and
(d) an aqueous carrier;

wherein the cationic surfactant and the polymer form a water-insoluble complex; and wherein the cationic surfactant and the high melting point fatty compound form a gel matrix.

The conditioning composition of the present invention provides improved conditioning benefits. The conditioner composition of the present invention can also provide improved hair setting benefits when a certain polymer is used.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Compositions

The composition of the present invention comprises by weight:
(a) from about 0.1% to about 10% of a cationic surfactant;
(b) from about 0.05% to about 10% of a water-soluble polymer selected from the group consisting of a water-soluble anionic polymer, a water-soluble amphoteric polymer, and mixtures thereof;
(c) from about 1.0% to about 10% of a high melting point fatty compound; and
(d) an aqueous carrier;

wherein the cationic surfactant and the polymer form a water-insoluble complex; and wherein the cationic surfactant and the high melting point fatty compound form a gel matrix.

The conditioning composition of the present invention can provide improved conditioning benefits. Without being limited to the theory, it is believed that; due to the deposition of the water-insoluble complex, i.e., coacervate on the substrates, the composition of the present invention provides improved conditioning benefits to wet substrates and provides improved conditioning to the substrates when they are dried. When a certain polymer is used, the composition of the present invention also provides improved styling benefits to the substrates when they are dried. It is also believed that, gel matrix is suitable for providing various conditioning benefits, especially slippery and slick application feel on wet substrates.

Without being limited to the theory, it is also believed that; when the composition of the present invention contains conditioning agents, the composition can provide further conditioning benefits due to sufficient deposition of conditioning agents. Without being limited to the theory, it is believed that; one preferred embodiment of the composition of the present invention is that containing conditioning agents which are dispersed in the composition and have a smaller particle size, since such agents are believed to be absorbed or adhered to the surface of the coacervates, or be incorporated into the coacervates, and then effectively deposit on the hair together with the coacervates.

The composition of the present invention can contain surfactants other than those described below under the title "CATIONIC SURFACTANT". In the composition of the present invention, it is preferred that the total amount of all surfactants in the composition is 10% or less by weight of the composition.

Preferably, in view of the compatibility with a gel matrix, the compositions of the present invention are substantially free of anionic surfactants. In the present invention, the compositions being "substantially free of anionic surfactants" means that the compositions include 2% or less, preferably 1% or less of anionic surfactants.

Cationic Surfactant

The compositions of the present invention comprise a cationic surfactant. The cationic surfactant is included in the compositions at a level of from about 0.1% to about 10.0%, preferably from about 0.5% to about 8.0%, more preferably from about 1% to about 8.0%.

A variety of cationic surfactants including mono-long alkyl quaternary ammonium salts, di-long alkyl quaternary ammonium salts, hydrophilically substituted mono-long alkyl quaternary ammonium salts, hydrophilically substituted di-long alkyl quaternary ammonium salts, mono-long alkyl chain amines, di-alkyl chain amines can be used in the compositions of the present invention as described below. Among them, preferred are mono-long alkyl chain cationic surfactants such as mono-long alkyl chain quaternary ammonium salts, hydrophilically substituted di-long alkyl quaternary ammonium salts, and mono-long alkyl chain amines. Highly preferred are cetyl trimethyl ammonium chloride, stearyl trimethyl ammonium chloride, behenyl trimethyl ammonium chloride, behenamidopropyldimethylamine, and stearamidopropyldimethylamine. Although these cationic surfactants are preferred in the present invention, other cationic surfactants such as di-long alkyl chain cationic surfactants may also be used alone, or in combination with such preferred cationic surfactants.

Cationic surfactants useful herein include, for example, those corresponding to the general formula (I):

wherein at least one of $R^{71}$, $R^{72}$, $R^{73}$ and $R^{74}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{71}$, $R^{72}$, $R^{73}$ and $R^{74}$ are independently selected from $C_1$ to about $C_{22}$ alkyl.

Among the cationic surfactants of general formula (I), preferred are those containing in the molecule at least one alkyl chain having at least 16 carbons. Non-limiting examples of such preferred cationic surfactants include: behenyl trimethyl ammonium chloride; cetyl trimethyl ammonium chloride; stearyl trimethyl ammonium chloride; olealkonium chloride; hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^{71}$-$R^{74}$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, dialkyloylethyl hydroxyethyl methyl ammonium salt, and mixtures thereof; for example, commercially available under the following tradenames; Dehyquart F75, Dehyquart L80, and Dehyquart C4046 from Croda. Babassuamidopropalkonium Chloride available from Croda under the tradename Incroquat BA-85 is also preferably used in the composition.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Water-Soluble Anionic or Amphoteric Polymer

The compositions of the present invention comprise a water-soluble polymer selected from a water-soluble anionic polymer, a water-soluble amphoteric polymer, and mixtures thereof. Water-soluble polymers are useful in the present invention compared to water-insoluble polymers, in view of formation of coacervates. The polymer is included in the compositions at a level by weight of from about 0.05% to about 10%, preferably from about 0.1% to about 5.0%.

The polymers useful herein are those having a molecular weight of preferably 1000 AMU (Atomic Mass Unit) or more. A variety of anionic polymers and amphoteric polymers can be used in the compositions of the present invention as described below.

Anionic polymers useful herein include, for example: Polyacrylic acid; Polymethacrylic acid; Carboxyvinylpolymer; acrylate copolymers such as Acrylate/C 10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; sulfonate polymers such as Polysulfonic acid, Polystyrene sulphonate, copolymers of methacrylic acid and acrylamidomethylpropane sulfonic acid, and copolymers of acrylic acid and acrylamidomethylpropane sulfonic acid; carboxymethylcellulose; carboxy guar gum; copolymers of ethylene and maleic acid; and acrylate silicone polymer. Neutralizing agents may be included to neutralize the anionic polymers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available highly preferred anionic polymers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic.

Amphoteric polymers useful herein include, for example, Polyquaternium-22, Polyquaternium-47, Polyquaternium-39, Octylacrylamide/Acrylates/Butylaminoethyl Methacrylate Copolymer, and Potato Starch modified. Commercially available highly preferred amphoteric polymers include, for example, Polyquaternium-39 having a tradename Merquat Plus 3330 available from Ondeo.

Coacervate

The above cationic surfactant and the above anionic and/or amphoteric polymers form coacervates which are water-insoluble complexes. Such coacervates can form in any of following conditions:
(i) when the cationic surfactant and the anionic and/or amphoteric polymers are mixed prior to the addition to gel matrix;
(ii) when the cationic surfactant and the anionic and/or amphoteric polymers are mixed in the composition; and
(ii) when the composition comprising the cationic surfactant and the anionic and/or amphoteric polymers is diluted with water, especially, when the composition is applied to wet substrate and/or rinsed-off with water from the substrate.

When coacervates form upon dilution of the composition, coacervates form when the mass ratio of the composition to water is, preferably by about 1:50, more preferably by about 1:20, still more preferably by about 1:10.

Without being limited to the theory, it is believed that such coacervates provide effective deposition on the substrate since the coacervates are water-insoluble. Without being limited to the theory, it is also believed that; when the composition of the present invention contains conditioning agents, especially preferred conditioning agents such as silicone emulsions having an average particle size of 500 nm or less, the composition can provide further conditioning benefits due to sufficient deposition of conditioning agents.

High Melting Point Fatty Compound

The compositions of the present invention comprise high melting point fatty compounds. The high melting point fatty compound is included in the composition at a level of from about 1% to about 10%, preferably from about 2% to about 8%, by weight of the composition.

The high melting point fatty compound useful herein have a melting point of 25° C. or higher, and is selected from the group consisting of fatty alcohols, fatty acids, fatty alcohol derivatives, fatty acid derivatives, and mixtures thereof. Among them, highly preferred are fatty alcohols. It is understood by the artisan that, depending on the number and position of double bonds, and length and position of the branches, certain compounds having certain required carbon atoms may have a melting point of less than 25° C. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The fatty alcohols useful herein are those having from about 14 to about 30 carbon atoms, preferably from about 16 to about 22 carbon atoms. These fatty alcohols are saturated and can be straight or branched chain alcohols. Non-limiting examples of fatty alcohols include, cetyl alcohol, stearyl alcohol, behenyl alcohol, and mixtures thereof.

Gel Matrix

The above cationic surfactant and the high melting point fatty compound form gel matrix together with aqueous carrier. Such gel matrix is suitable for providing various conditioning benefits, especially, spreadability on wet substrates and slippery and slick application feel on wet substrates. Such gel matrix can be used as the thickening agent and is suitable for providing suitable viscosity and rheology for conditioning compositions.

It is preferred that, in gel matrix, the cationic surfactant and the high melting point fatty compound are contained at a level such that the mole ratio of the cationic surfactant to the high melting point fatty compound is in the range of from about 1:1 to about 1:10, more preferably from about 1:2 to about 1:6, in view of providing improved slippery and slick application feel on wet substrates.

Aqueous Carrier

The compositions of the present invention comprise an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 60% to about 99%, preferably from about 70% to about 98%, and more preferably from about 75% to about 95% water.

The pH of the present compositions are preferably from about 2 to about 8, more preferably from about 3 to about 7. Buffers and other pH adjusting agents can be included to achieve the desirable pH.

Thickening Polymer

The composition of the present invention may contain a thickening polymer. Thickening polymers useful herein are those which can help the composition provide appropriate viscosity and rheology properties to the composition. The composition of the present invention can contain a thickening polymer at a level by weight of preferably from about 0.01% to about 10%, more preferably from about 0.05% to about 5%, still more preferably from about 0.1% to about 3%, even more preferably from about 0.5% to about 2%.

A variety of thickening polymers can be used in the compositions of the present invention. Thickening polymers useful herein include, for example, cellulose and its derivatives such as cellulose ethers including hydroxyethylcellulose and hydroxypropylcellulose, hydrophobically modified cellulose ethers such as cetyl hydroxyethylcellulose which is supplied, for example, by Hercules with a tradename Polysurf 67, quaternized celluloses, and hydrophobically modified cationic celluloses; guar polymers including cationic guar polymers and nonionic guar polymers such as Guar Gum 2-hydroxypropyl ether which is supplied, for example, by Rhodia with a tradename Jaguar HP-105; crosslinked polymers such as nonionic crosslinked polymers and cationic crosslinked polymers; and acrylate polymers such as sodium polyacrylate, polyethylacrylate, polyacrylamide, and hydrophobically modified crosslinked cationic acrylates. The thickening polymers useful herein may include the polymers disclosed below under the title "Cationic polymer". Among a variety of thickening polymers, highly preferred are nonionic and thickening polymers such as nonionic guar polymers, hydroxyethylcellulose, hydroxypropylcellulose, and hydrophobically modified cellulose ethers such as cetyl hydroxyethylcellulose. Especially preferred are hydrophobically modified cellulose ethers such as cetyl hydroxyethylcellulose.

Conditioning Agent

The compositions of the present invention preferably contain a conditioning agent. The conditioning agents can be included in the compositions at a level by weight of from about 0.1% to about 20%, more preferably from about 0.1% to about 15%, still more preferably from about 0.25% to about 10%.

The conditioning agent useful herein include, for example, silicone compounds, glycerin, polyglycerin having a molecular weight of less than about 600,000 AMU, polyglycerin esters having a molecular weight of less than about 600,000 AMU, polyoxyalkylene glycols having a molecular weight of from about 1,000 AMU to about 600,000 AMU such as polyethylene glycols and polypropylene glycols, hydrocarbons, fatty compounds other than those described above under the title "HIGH MELTING POINT FATTY COMPOUND", and mixtures thereof. The conditioning agents useful herein are preferably cationic or nonionic. In view of obtaining sufficient deposition of conditioning agents, it is preferred that conditioning agents is in a form of emulsion having an average particle size of 500 nm or less, preferably 300 nm or less, more preferably 100 nm or less when contained in the composition.

Silicone Compound

The conditioning agent used in the present invention is preferably a silicone compound. The silicone compound can be included in the compositions at levels by weight of, preferably from about 0.1% to about 10%, more preferably from about 0.5% to about 8%, still more preferably from about 1% to about 5%.

(i) Silicone Emulsion

In view of obtaining sufficient deposition of conditioning agents, it is preferred that conditioning agents is in a form of emulsion having an average particle size of 500 nm or less, preferably 300 nm or less, more preferably 100 nm or less when contained in the composition.

Commercially available silicone emulsions useful herein include, for example, that with a tradename Silicone DC-8177, DC-1870, DC8168, DC8194 and DC7113 available from Dow Corning; quaternized silicone emulsion with a tradename DC5-7133 available from Dow Corning; and amodimethicone emulsion with a tradename XS65-B6413 and SME253 available from General Electric and ADM8020 available from Wacker. Such silicone emulsions may contain a certain level of anionic surfactants. In such case, it is preferred that the composition include 2% or less, more preferably 1% or less of anionic surfactants, as described above under the title "COMPOSITIONS".

(ii) Substantially Soluble Silicones

Other silicone compounds are also useful herein. Such silicone compounds include, for example, following materials which can be substantially soluble depending on the level of hydrophilic groups in their structure: silicone copolyols such as dimethicone copolyols, for example those having a tradename Silsoft 475, Silsoft 870 and Silsoft 810 available from GE Silicone, and those having DC5330 available from Dow Corning; amino silicones such as those having a amine content which is high enough to make the amino silicones substantially soluble; amino silicone copolyols such as those having an INCI name Bis (C13-15 Alkoxy) PG Amodimethicone available with a tradename DC2-8500 from Dow Corning; hydrophobically modified amino silicone copolyols; hydrophobically modified amido silicone copolyols such as those having an INCI name PEG-12 Methyl Ether/Lauroxy PEG-5 Amidopropyl Dimethicone available from Dow Corning; and quaternized silicones.

(iii) Other Silicones

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferably, the silicone compounds have an average particle size of from about 1 microns to about 50 microns, in the composition.

The silicone compounds useful herein include polyalkyl or polyaryl siloxanes with the following structure:

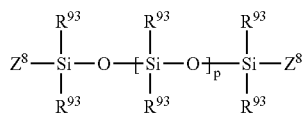

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000 AMU, generally between about 200,000 AMU and about 1,000,000 AMU. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These materials are also known as dimethicone copolyols.

Silicone compounds useful herein also include amino substituted materials. Preferred aminosilicones include, for example, those which conform to the general formula (I):

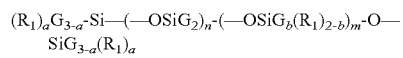

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —$N(R_2)CH_2$—$CH_2$—$N(R_2)_2$; —$N(R_2)_2$; —$N(R_2)_3A^-$; —$N(R_2)CH_2$—$CH_2$—$NR_2H_2A^-$;

wherein $R_2$ is hydrogen, phenyl, benzyl, or a saturated hydrocarbon radical, preferably an alkyl radical from about $C_1$ to about $C_{20}$; $A^-$ is a halide ion.

One highly preferred amino silicones are those corresponding to formula (III) wherein m=0, a=1, q=3, G=methyl, n is preferably from about 1500 to about 1700, more preferably 1600; and L is —$N(CH_3)_2$ or —$NH_2$, more preferably —$NH_2$. Another highly preferred amino silicones are those corresponding to formula (III) wherein m=0, a=1, q=3, G=methyl, n is preferably from about 400 to about 600, more preferably about 500; and L is —$N(CH_3)_2$ or —$NH_2$, more preferably —$NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those represented by the following structure:

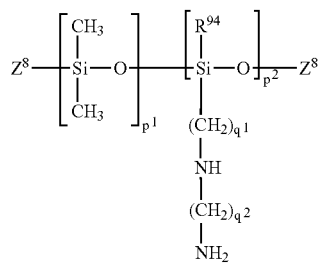

wherein $R^{94}$ is H, $CH_3$ or OH; $p^1$ and $p^2$ are integers of 1 or above, and wherein sum of $p^1$ and $p^2$ is from 650 to 1,500; $q^1$ and $q^2$ are integers of from 1 to 10. $Z^8$ represents groups which block the ends of the silicone chains. Suitable $Z^8$ groups include hydroxy, methyl, methoxy, ethoxy, propoxy, and aryloxy. Highly preferred are those known as "amodimethicone". Commercially available amodimethicones useful herein include, for example, BY16-872 available from Dow Corning.

Cationic Polymer

The conditioning compositions of the present invention may further include cationic polymers for obtaining further improved conditioning benefits and for helping the deposition of coacervates. The cationic polymers hereof will generally have a weight average molecular weight which is at least about 1,000 AMU, and is less than about 30 million AMU.

The cationic polymer can be included in the compositions at a level by weight of preferably from about 0.01% to about 10%, more preferably from about 0.05% to about 5%, still more preferably from about 0.05% to about 2.0%.

Suitable cationic polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, Polyquaternium-7 including that commercially available with tradenames Merquat 550 and Merquat S from Ondeo Nalco; polymethacrylamidopropyl trimonium chloride such as that commercially available with a tradename Polycare 133 from Rhone-Poulenc; and Polyquaternium-37 available from 3V Sigma with tradenames Synthalen CR, Synthalen CU, and Synthalen CN.

Also suitable cationic polymers herein include cationic cellulose derivatives. Cationic cellulose derivative useful herein include, for example, salts of hydroxyethyl cellulose reacted with trimethyl ammonium substituted epoxide, referred to in the industry (CTFA) as Polyquaternium 10, available from Amerchol Corp. (Edison, N.J., USA) in their Polymer JR® and LR® series, and also available from National Starch & Chemical with a tradename Celquat SC-230M; and Polyquaternium-4 with tradename Celquat H-100 available from National Starch & Chemical.

Other suitable cationic polymers include cationic guar gum derivatives, such as guar hydroxypropyltrimonium chloride commercially available from Rhodia in their Jaguar series.

Additional Components

The compositions of the present invention may include additional components, which may be selected by the artisan according to the desired characteristics of the final product and which are suitable for rendering the compositions more cosmetically or aesthetically acceptable or to provide them with additional usage benefits. Such additional components generally are used individually at levels of from about 0.001% to about 10%, preferably from about 0.01% to about 5% by weight of the composition.

Co-solvent

The compositions of the present invention may contain a co-solvent to help the components such as coacervates, surfactants, silicone compounds, and perfumes if included, to be substantially soluble/dispersible in the composition. The co-solvents useful herein are selected from the group consisting of polyhydric alcohols, water soluble alkoxylated nonionic polymers, water-soluble alkyl alcohols and ethers and mixtures thereof. The co-solvents herein can be used at levels by weight of the compositions of preferably from about 0.1% to about 50%, more preferably from about 0.1% to about 20%, still more preferably from about 0.5% to about 10%.

Polyhydric alcohols useful herein include, for example, glycerin, sorbitol, propylene glycol, butylene glycol, hexylene glycol, ethoxylated glucose, 1,2-hexane diol, hexanetriol, 1,5-pentane diol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, octyne diol, diethylene glycol, and mixtures thereof.

Water soluble alkoxylated nonionic polymers useful herein include, for example, polyethylene glycols and polypropylene glycols having a molecular weight of up to about 10,000 AMU such as those with CTFA names PEG-4, PEG-8, PEG-12, PEG-20, PEG-150 and mixtures thereof.

Water soluble alkyl alcohols useful herein include, for example, monohydric C1-C6 alkyl alcohols such as ethanol, isopropyl alcohol, propanol and benzyl alcohol. Water soluble ethers useful herein include, for example, 2-butoxy ethanol, monomethyl ether of diethylene glycol, monoethyl ether of diethylene glycol, monobutyl ether of diethylene glycol.

Among a variety of co-solvents, preferred are 1,2-hexane diol, hexylene glycol, butylene glycol, glycerine, isopropyl alcohol, ethanol, propylene glycol, 1,5-pentane diol, and mixtures thereof.

Electrolyte

The compositions of the present invention may contain an electrolyte to control degree of coacervate formation in the composition. The electrolyte can be used at levels by weight of the compositions of, preferably from about 0.05% to about 10%, more preferably from about 0.1% to about 5.0%.

The electrolytes useful herein are salts, and such salts useful herein include, for example, chlorides, bromides and nitrates of alkali metals, alkaline earth metals and ammonium. Preferred salts are selected from the group consisting of sodium chloride, sodium bromide, sodium nitrate, potassium chloride, potassium bromide, calcium chloride, magnesium chloride, and ammonium chloride, and mixtures thereof.

Other Additional Components

A wide variety of additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, nonionic surfactants such as glyceryl stearate available from Stepan Chemicals, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; ultraviolet and infrared screening and absorbing agents such as octyl salicylate; antidandruff agents such as zinc pyrrithione and salicylic acid.

Product Forms

The conditioning compositions of the present invention can be in the form of rinse-off products or leave-on products, can be opaque, and can be formulated in a wide variety of product forms, including but not limited to creams, gels, emulsions, mousses and sprays.

The conditioning compositions of the present invention can be used for conditioning a variety of substrates such as hair, skin, and fabric, by applying the compositions to the substrates such as hair, skin, and fabric. The conditioning compositions of the present invention is especially suitable for hair care products such as hair conditioners, skin care products such as skin conditioners, and fabric care products such as fabric softeners.

The conditioning compositions of the present invention are especially suitable for hair conditioners for rinse-off use. Such compositions are preferably used by following steps:

(i) after shampooing hair, applying to the hair an effective amount of the conditioning compositions for conditioning the hair; and
(ii) then rinsing the hair.

Method of Preparation

Preferably, the composition of the present invention can be prepared by a method of preparation comprising the steps of:
(a) preparing a coacervate comprising the steps of:
  (a1) mixing a part of the cationic surfactant and the water-soluble polymer in a part of aqueous carrier to form a coacervate;
(b) preparing a gel matrix comprising the step of:
  (b1) mixing the rest of the cationic surfactant, the high melting point fatty compound, and the rest of aqueous carrier at a temperature of from about 80° C. to about 90° C. until the components are homogenized, and no solids are observed;
  (b2) the mixture is then cooled to from about 50° C. to about 60° C. and maintained at this temperature to form a gel matrix;
(c) mixing the coacervate and the gel matrix.

While not essential to the present method, conditioning agents such as silicones are preferably added. When added, it is preferred that conditioning agents such as silicones be added to the gel matrix or incorporated into coacervate by mixing together with the cationic surfactant and the water-soluble polymer. Other components such as preservatives and perfumes, when included, can be included, for example, after the coacervate and the gel matrix are mixed.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

| Compositions (wt %) | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Anionic polymer-1 *1 | 0.25 | — | — | 0.25 | — | 2.0 | — | — | 0.5 |
| Anionic polymer-2 *2 | — | 0.25 | — | — | — | — | — | — | — |
| Anionic polymer-3 *3 | — | — | 0.25 | — | 0.5 | — | 2.0 | — | — |
| Anionic polymer-4 *4 | — | — | — | — | — | — | — | 0.25 | — |
| Cationic surfactant-1 *5 | — | 1.0 | 1.0 | 1.0 | 1.0 | 1.5 | 3.0 | — | 1.0 |
| Cationic surfactant-2 *6 | — | 3.4 | 3.5 | — | 3.4 | — | — | 3.5 | — |
| Cationic surfactant-3 *7 | 3.0 | — | — | 2.0 | — | 2.0 | 4.0 | — | 2.0 |
| Cationic surfactant-4 *8 | — | — | — | — | — | — | — | 1.0 | — |
| Nonionic surfactant-1 *10 | — | — | — | — | 1.0 | — | — | — | — |
| Nonionic surfactant-2 *11 | — | — | 3.0 | — | — | — | 2.5 | 3.0 | — |
| Thickening polymer-1 *13 | — | — | — | 1.2 | 1.2 | — | — | — | — |
| Thickening polymer-2 *14 | — | — | — | — | — | — | — | — | 2.0 |
| Dimethicone gum/cyclopentasiloxane blend *18 | — | — | — | 2.0 | — | 2.0 | — | — | — |
| Aminosilicone *19 | — | — | — | — | — | — | — | — | 2.0 |
| Hydrophobically modified amidomethicone copolyol *20 | — | — | 4.2 | — | — | — | — | — | — |
| Quaternized silicone emulsion *21 | 4.2 | 8.0 | — | — | 2.0 | 2.0 | 0.5 | 4.2 | — |
| Cetyl Alcohol | 2.5 | 2.3 | 2.0 | 2.5 | 2.0 | 5.5 | 3.0 | 2.0 | 2.5 |
| Stearyl Alcohol | 4.5 | 4.2 | 3.5 | 4.5 | 3.6 | 4.5 | 7.0 | 3.5 | 4.5 |
| PEG-200 | — | — | — | — | 1.0 | — | — | — | — |
| L-glutamic acid | 0.3 | — | — | 0.6 | — | 0.9 | 1.2 | — | 0.6 |
| Methylchloroisothiazolinone/Methylisothiazolinone *22 | 0.001 | 0.001 | 0.001 | 0.001 | 0.001 | 0.001 | 0.001 | 0.001 | 0.001 |
| Sodium Chloride | — | — | — | 1.0 | 1.0 | — | — | — | 1.0 |

-continued

| Compositions (wt %) | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Disodium EDTA | 0.1 | 0.13 | 0.13 | 0.13 | 0.13 | 0.1 | — | — | 0.13 |
| m-Paraben | — | — | — | 0.2 | 0.2 | — | — | — | 0.2 |
| Benzyl alcohol | 0.4 | 0.4 | 0.4 | — | — | 0.4 | 0.4 | 0.4 | — |
| Perfume | 0.3 | 0.01 | 0.3 | 0.7 | 0.4 | 0.3 | 0.01 | 0.7 | 0.3 |
| Deionized water | | | | - q.s. to 100% - | | | | | |

| Compositions (wt %) | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|
| Anionic polymer-1 *1 | 0.25 | — | — | — | — | 2.0 | — | — | 0.5 |
| Anionic polymer-2 *2 | — | 0.5 | — | — | — | — | — | — | — |
| Anionic polymer-3 *3 | — | — | 1.0 | — | 0.5 | — | — | — | — |
| Anionic polymer-4 *4 | — | — | — | 1.0 | — | — | 0.5 | 2.0 | — |
| Cationic surfactant-1 *5 | — | 1.0 | — | — | 1.0 | 1.0 | 3.0 | — | 1.0 |
| Cationic surfactant-2 *6 | 1.0 | — | — | — | 1.5 | — | — | 3.5 | — |
| Cationic surfactant-3 *7 | — | — | — | 2.0 | — | — | 4.0 | — | 2.0 |
| Cationic surfactant-4 *8 | 1.0 | 0.5 | 2.0 | — | — | 3.0 | — | 1.0 | — |
| Cationic surfactant-5 *9 | — | — | 1.0 | 1.0 | — | — | — | — | — |
| Nonionic surfactant-1 *10 | — | — | — | — | 1.0 | — | — | — | — |
| Nonionic surfactant-2 *11 | — | — | — | 3.0 | — | — | — | 2.5 | 3.0 |
| Nonionic surfactant-3 *12 | — | 1.0 | — | — | — | — | 2.0 | — | — |
| Thickening polymer-1 *13 | — | — | — | 1.0 | — | — | — | — | — |
| Thickening polymer-2 *14 | — | — | — | — | — | — | — | 1.0 | — |
| Thickening polymer-3 *15 | — | — | — | — | 0.5 | — | — | — | — |
| Thickening polymer-4 *16 | — | — | — | — | — | — | — | — | 1.0 |
| Thickening polymer-5 *17 | 1.0 | — | 0.5 | — | — | — | — | — | — |
| Aminosilicone *19 | 1.5 | — | — | — | — | 2.0 | 1.0 | — | — |
| Hydrophobically modified amidomethicone copolyol *20 | — | — | — | 3.6 | — | — | — | — | 2.0 |
| Quaternized silicone emulsion *21 | — | 3.3 | 1.0 | — | 1.5 | 2.0 | — | 4.2 | — |
| Cetyl Alcohol | 0.4 | 1.0 | 1.0 | 0.8 | 0.5 | 0.6 | 0.3 | 0.4 | 1.0 |
| Stearyl Alcohol | 0.8 | 1.5 | 1.0 | 1.0 | 0.7 | 0.8 | 04 | 0.9 | 1.2 |
| PEG-200 | — | — | — | — | 1.0 | — | — | — | — |
| L-glutamic acid | 0.9 | — | — | — | 0.6 | — | 0.6 | 1.2 | 0.6 |
| Methylchloroisothiazolinone/Methylisothiazolinone *22 | 0.001 | 0.001 | 0.001 | 0.001 | 0.001 | 0.001 | 0.001 | 0.001 | 0.001 |
| Sodium Chloride | — | — | — | 1.0 | 1.0 | — | — | — | 1.0 |
| Disodium EDTA | 0.1 | 0.13 | 0.13 | 0.13 | 0.13 | 0.1 | — | — | 0.13 |
| m-Paraben | — | — | — | 0.2 | 0.2 | — | — | — | 0.2 |
| Benzyl alcohol | 0.4 | 0.4 | 0.4 | — | — | 0.4 | 0.4 | 0.4 | — |
| Perfume | 0.3 | 0.01 | 0.3 | 0.7 | 0.4 | 0.3 | 0.01 | 0.7 | 0.3 |
| Deionized water | | | | - q.s. to 100% - | | | | | |

Definitions of Components
*1 Anionic polymer-1: Carbomer having a tradename Carbopol 980 available from Noveon
*2 Anionic polymer-2: Carbomer having a tradename Carbopol 981 available from Noveon
*3 Anionic polymer-3: Sodium Carboxymethylcellulose having a tradename CMC9M31CFPH available from Hercules
*4 Anionic polymer-4: Sodium Polystyrene Sulfonate having a tradename FLEXAN II available from National Starch
*5 Cationic surfactant-1: Cetrimonium Chloride
*6 Cationic surfactant-2: Stearyltrimonium Chloride
*7 Cationic surfactant-3: Behenyltrimonium Chloride
*8 Cationic surfactant-4: Stearamidopropyldimethylamine
*9 Cationic surfactant-5: Dicocoylethyl hydroxyethyl methyl ammonium methosulfate having a tradename Dehyquart L80 available from Croda
*10 Nonionic surfactant-1: Ceteth-20 having a tradename Nikkol BC-20TX available from Nikko Chemicals
*11 Nonionic surfactant-2: Laureth-9
*12 Nonionic surfactant-3: PEG-7 Caprylic/Capric Glyceride having a tradename Cetiol HE810 available from Cognis
*13 Thickening polymer-1: Guar Gum 2-Hydroxypropyl Ether having a tradename Jaguar HP-105 available from Rhodia
*14 Thickening polymer-2: Hydroxyethyl ethyl cellulose having a tradename Elfacos CD481 available from Akozo Novel.
*15 Thickening polymer-3: Cetyl hydroxyethyl cellulose having a tradename Polysurf 67 available from Hercules
*16 Thickening polymer-4: Hydroxyethyl cellulose having a tradename Natrosol from Hercules
*17 Thickening polymer-5: Hydorxypropyl cellulose having a tradename Klucel form CP Kelco
*18 Dimethicone gum/cyclopentasiloxane blend: supplied by GE Silicone as a blend of dimethicone having a viscosity if 18,000,000 mPa · s and cyclopentasiloxane
*19 Aminosilicone: Available from GE having a viscosity 10,000 mPa · s, and having following formula (I):
$(R_1)_a G_{3-a} - Si - (-OSiG_2)_n - (-OSiG_b(R_1)_{2-b})_m - O - SiG_{3-a}(R_1)_a$ (I)
wherein G is methyl; a is an integer of 1; b is 0, 1 or 2, preferably 1; n is a number from 400 to about 600; m is an integer of 0; $R_1$ is a monovalent radical conforming to the general formula $C_qH_{2q}L$, wherein q is an integer of 3 and L is $-N(CH_3)_2$
*20 Hydrophobically modified amidomethicone copolyol: PEG-12 Methyl Ether/Lauroxy PEG-5 Amidopropyl Dimethicone available from Dow Corning
*21 Quaternized silicone emulsion: DC5-7133 available from Dow Corning
*22 Methylchloroisothiazolinone/Methylisothiazolinone: Kathon CG available from Rohm&Haas Method of Preparation The conditioning compositions of "Ex.1" to "Ex.18" as shown above can be prepared by any conventional method well known in the art. Especially, the compositions of "Ex.1" through "Ex.3", "Ex.6" through "Ex.8", "Ex.11", "Ex.15", and "Ex.16" are suitably made as follows:

(a) preparing a coacervate comprising the steps of:
   (a1) mixing a part of the cationic surfactant and the water-soluble polymer in a part of aqueous carrier to form a coacervate;

(b) preparing a gel matrix comprising the step of:
   (b1) mixing the rest of the cationic surfactant, the high melting point fatty compound, and the rest of aqueous carrier at a temperature of from about 80° C. to about 90° C. until the components are homogenized, and no solids are observed;
   (b2) the mixture is then cooled to from about 50° C. to about 60° C. and maintained at this temperature to form a gel matrix;

(c) mixing the coacervate and the gel matrix.

Other components such as silicones, preservatives, and perfumes, when included, can be added to the mixture of the coacervate and the gel matrix.

The compositions of "Ex.4", "Ex.5", "Ex.9", "Ex.10", "Ex.12" through "Ex.14", "Ex.17" and "Ex.18", all containing a thickening polymer, are suitably made as follows:

(a) preparing a first mixture comprising the steps of:
   (a1) mixing the cationic surfactant-1, nonionic surfactants, the water-soluble polymer, the thickening polymer, and silicones in a part of aqueous carrier;

(b) preparing a second mixture being gel matrix comprising the step of:
   (b1) mixing the rest of the cationic surfactant-2 or 3, the high melting point fatty compound, and the rest of aqueous carrier at a temperature of from about 80° C. to about 90° C. until the components are homogenized, and no solids are observed;
   (b2) the mixture is then cooled to from about 50° C. to about 60° C. and maintained at this temperature to form a gel matrix;

(c) mixing the first mixture and the second mixture.

Other components such as preservatives and perfumes, when included, can be added after the fist and the second mixtures are mixed.

Examples 1 through 18 are conditioning compositions of the present invention which are particularly useful for hair conditioners for rinse-off use. These examples have many advantages. For example, the compositions of "Ex.1" through "Ex.18" provide conditioning benefits due to the deposition of coacervates. The compositions also provide various conditioning benefits, especially slippery and slick application feel on wet hair, due to gel matrix.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of preparation of a conditioning composition comprising the steps of:
   (a) preparing a coacervate comprising the steps of:
     (a1) mixing a part of from about 0.1% to about 10% of a cationic surfactant and from about 0.05% to about 10% of a water-soluble polymer selected from the group consisting of a water-soluble anionic polymer, a water-soluble amphoteric polymer, and mixtures thereof, in a part of an aqueous carrier to form a coacervate;
   (b) preparing a gel matrix comprising the step of:
     (b1) mixing the rest of the cationic surfactant, a high melting point fatty compound, and the rest of aqueous carrier at a temperature of from about 80° C. to about 90° C. until the components are homogenized, and no solids are observed;
     (b2) the mixture is then cooled to from about 50° C. to about 60° C. and maintained at this temperature to form a gel matrix;
   (c) mixing the coacervate and the gel matrix.

* * * * *